US010639187B2

United States Patent
Simonetti

(10) Patent No.: US 10,639,187 B2
(45) Date of Patent: May 5, 2020

(54) APPARATUS AND METHOD FOR REDUCING BRUXISM AND OCCLUSAL FORCES

(71) Applicant: ADVANCED FACIALDONTICS LLC, St. James, NY (US)

(72) Inventor: Scott A. Simonetti, East Islip, NY (US)

(73) Assignee: Advanced Facialdontics LLC, St. James, NY (US)

( * ) Notice: Subject to any disclaimer, the term of this patent is extended or adjusted under 35 U.S.C. 154(b) by 465 days.

(21) Appl. No.: 15/492,643

(22) Filed: Apr. 20, 2017

(65) Prior Publication Data

US 2017/0304108 A1    Oct. 26, 2017

Related U.S. Application Data

(60) Provisional application No. 62/325,176, filed on Apr. 20, 2016, provisional application No. 62/325,185,
(Continued)

(51) Int. Cl.
*A61F 5/56* (2006.01)
*A61C 7/10* (2006.01)
*A61C 7/08* (2006.01)

(52) U.S. Cl.
CPC ............... *A61F 5/566* (2013.01); *A61C 7/08* (2013.01); *A61C 7/10* (2013.01); *A61F 2005/563* (2013.01)

(58) Field of Classification Search
CPC ...... A61F 5/566; A61F 2005/563; A61F 5/56; A61F 5/58; A61F 5/0102; A61F 2005/0137; A61F 2005/0139; A61F 2005/0153; A61F 5/026; A61F 5/028; A61F 2210/009; A61F 2250/0067; A61F 2/0022; A61F 2/28; A61F 2/30; A61F 2/36; A61F 2/94; A61F 5/0125; A61F 5/055; A61F 2002/9528; A61F 2250/0004; A61F 2250/0065; A61F 2/013; A61F 2/14; A61F 2/82; A61F 2/95; A61F 5/013; A61F 9/007; A61F 9/00727; A61C 7/08; A61C 7/10; A61C 19/063;
(Continued)

(56) References Cited

U.S. PATENT DOCUMENTS 4,026,023 A    5/1977 Fisher
4,239,487 A    12/1980 Murdock
(Continued)

OTHER PUBLICATIONS

PCT International Preliminary Report on Patentability dated Jun. 13, 2018, corresponding to PCT Application No. PCT/US2017/028593.
(Continued)

*Primary Examiner* — Tarla R Patel
(74) *Attorney, Agent, or Firm* — George Likourezos; Carter, DeLuca & Farrell LLP

(57) ABSTRACT

An orthotic device for redefining an occlusal plane includes a left portion, a right portion including an upper surface, a bite block coupled to either the left portion or the right portion, and a lingual portion coupled to the left portion and the right portion. The orthotic device is configured to engage teeth located along a left portion and a right portion of a mandible. The bite block is disposed along the upper surface of either the left portion or the right portion and extends upward relative to an upper surface of the left or right portion.

14 Claims, 12 Drawing Sheets

Related U.S. Application Data filed on Apr. 20, 2016, provisional application No. 62/325,192, filed on Apr. 20, 2016.

(58) Field of Classification Search
CPC ... A61B 5/4547; A61B 5/4552; A61B 5/4557; A61B 5/682; A61B 5/0534; A63B 71/085; A63B 2071/086; A63B 2017/088; Y10S 602/902; A61N 2/00; A61N 2/002; A61N 2/004; A61N 2/006; A61N 2/008; A61N 1/40; G09B 19/003; G09B 23/28; Y10T 29/49826
See application file for complete search history.

(56) References Cited

U.S. PATENT DOCUMENTS

| | | |
|---|---|---|
| 4,433,956 A | 2/1984 | Witzig |
| 4,439,149 A | 3/1984 | Devincenzo |
| 4,457,708 A | 7/1984 | Dufour |
| 4,609,349 A | 9/1986 | Cain |
| 5,002,485 A | 3/1991 | Aagesen |
| 5,080,584 A | 1/1992 | Karabin |
| 5,163,840 A | 11/1992 | Bourke |
| 5,324,196 A | 6/1994 | Magill |
| 5,443,384 A | 8/1995 | Franseen et al. |
| 5,536,168 A | 7/1996 | Bourke |
| 5,540,687 A | 7/1996 | Fairley et al. |
| 5,683,244 A | 11/1997 | Truax |
| 5,795,150 A | 8/1998 | Boyd |
| 5,848,981 A | 12/1998 | Herbranson |
| 6,096,079 A | 8/2000 | Eaton |
| 6,099,304 A | 8/2000 | Carter |
| 6,334,771 B1 | 1/2002 | Liou |
| 6,435,870 B1 | 8/2002 | Walde |
| 7,314,372 B2 | 1/2008 | Belfor et al. |
| 7,357,635 B2 | 4/2008 | Belfor et al. |
| D600,350 S | 9/2009 | Singh |
| 7,794,399 B2 | 9/2010 | Singh |
| 7,887,324 B2 | 2/2011 | Singh |
| D636,083 S | 4/2011 | Singh |
| 8,192,196 B2 | 6/2012 | Singh |
| D704,843 S | 5/2014 | Singh |
| D713,530 S | 9/2014 | Singh |
| D731,659 S | 6/2015 | Singh |
| D736,945 S | 8/2015 | Singh |
| 2007/0283967 A1 | 12/2007 | Bailey |
| 2007/0292819 A1* | 12/2007 | Scarberry ............... A61F 5/566 433/140 |
| 2009/0038403 A1 | 2/2009 | Kamei et al. |
| 2009/0308403 A1 | 12/2009 | Roettger et al. |
| 2011/0269095 A1* | 11/2011 | Singh .................. A61C 7/10 433/24 |
| 2011/0308532 A1* | 12/2011 | Nelissen ................. A61C 7/36 128/848 |
| 2016/0015556 A1* | 1/2016 | Luco ..................... A61F 5/566 128/848 |
| 2016/0184129 A1* | 6/2016 | Liptak ................... A61F 5/566 128/848 |
| 2017/0196727 A1* | 7/2017 | Giridharagopalan ... A61F 5/566 |

OTHER PUBLICATIONS

PCT International Search Report and Writtten Opinion for PCT/US2017/028593 dated Jul. 17, 2017.

Homeoblock & DNA Appliance Review—Adult Palate Expansion Device, https://web.archive.org/web/20141023052918/http://claimingpower.com/homeoblock-dna-appliance-review/ Publication date: Aug. 18, 2014.

PCT Written Opinion of the International Preliminary Examining Authority corresonding to PCT Application No. PCT/US2017/028593 dated Mar. 8, 2018, 17 pages.

\* cited by examiner

APPARATUS AND METHOD FOR REDUCING BRUXISM AND OCCLUSAL FORCES

CROSS-REFERENCE TO RELATED APPLICATIONS

The present application claims the benefit of U.S. Provisional Patent Application No. 62/325,176, filed on Apr. 20, 2016, entitled "PREVENTIVE ORAL DEVICE (POD)", U.S. Provisional Patent Application No. 62/325,192, filed on Apr. 20, 2016, entitled "RETAINER APPLIANCE", and U.S. Provisional Patent Application No. 62/325,185, filed on Apr. 20, 2016, entitled "ORAL ORTHOTIC APPLIANCE (NIGHTBLOCK)", the entire contents of each of which are incorporated by reference herein.

TECHNICAL FIELD

The present disclosure relates to apparatuses and methods for protecting a patient's teeth from damaging parafunctional occlusal forces, such as clenching and grinding. More specifically, the present disclosure relates to oral orthotic inserts which, when positioned in an individual's mouth, redefine the patient's occlusal plane to protect the teeth from bruxism and reduce occlusal forces.

BACKGROUND

Orthodontic apparatuses, methods, and procedures can be used to correct a variety of oral health issues. Orthodontic cases (braces) have been used to align an individual's teeth to repair abnormalities in the individual's tooth arrangement. Once braces are removed, retainers such as Hawley retainers are fitted for the individual to prevent the individual's teeth from moving after repositioning.

To correct other or deficiencies, such as cross-bites, a narrow maxillary or mandibular bone, clenching, grinding, or other oral conditions, apparatuses may be installed temporarily or permanently for varying periods of time to address such conditions, such as palate expanders, mandibular splints and bite plates, or retainers.

SUMMARY

The present disclosure relates to an oral orthotic device for redefining an occlusal plane. The oral orthotic includes a left portion and a right portion including an upper surface, a bite block coupled to either the left portion or the right portion, and a lingual portion coupled to the left portion and the right portion. The bite block is disposed along the upper surface of either the left portion or the right portion and extends upward relative to an upper surface of the left portion or the right portion. The unilateral bite block may be placed at the position of the first mandibular molar and second mandibular premolar.

In aspects, the bite block extends upward between two and seven millimeters from an occlusal plane defined by teeth of a patient. The orthotic device may further include a first wire enclosed along the lingual portion and configured to apply counter force when torsional force is applied to the orthotic. The orthotic device may further include a second wire braided about the first wire.

According to aspects, the left portion defines a left arc and the right portion defines a right arc. The left arc is configured to contour to teeth located along a left portion of a mandible, and the right arc is configured to contour to teeth located along a right portion of the mandible. The left arc and right arc may be dimensioned to contour teeth located in a mouth of a patient.

The present disclosure further relates to a retainer appliance which redefines an occlusal plane. The retainer appliance includes a retainer body including a frame extending therefrom, a left clasp extending from a left portion of the body and configured to couple to teeth located in a mouth of a patient, a right clasp extending from a right portion of the body, and a bite block coupled to either the left clasp or the right clasp. The bite block may enclose either the left clasp or the right clasp and extends toward opposing teeth located in the mouth of the patient.

According to aspects, the bite block extends toward opposing teeth between two and seven millimeters from an occlusal plane defined by teeth of the patient. The retainer body includes a left portion and a right portion. The retainer appliance may further include a spacer mechanism coupling to the left portion and the right portion of the retainer body. The spacer mechanism may further include a screw configured to expand or contract a gap between the left portion of the retainer mechanism and the right portion of the retainer mechanism.

The present disclosure also relates to a method of augmenting an occlusal plane with an orthotic device. The method includes providing an orthotic device to a patient, the orthotic device having a left portion, a right portion, a lingual portion, and a bite block positioning the orthotic device in a mouth of the patient, and applying pressure to the orthotic device to cause the left portion and the right portion to engage teeth located along a mandible of the patient.

According to aspects, the method may further include removing the orthotic device from the mouth of the patient, augmenting a height of the bite block. The height of the bite block may be adjusted in response to visual inspection of the orthotic when located in the mouth of the patient.

Additionally, the present disclosure relates to a method of augmenting an orthotic plane with a retainer appliance. The method includes providing a retainer appliance to an individual, the retainer appliance having a retainer body including a frame extending therefrom, a left clasp, a right clasp, and a bite block enclosing either the left clasp or the right clasp, positioning the retainer appliance in a mouth of a patient, applying pressure to the retainer appliance to cause the left clasp and the right clasp to engage teeth located along a maxilla of the patient.

According to aspects, the method further includes removing the retainer appliance from the mouth of the patient, and augmenting the height of the bite block. The height of the bite block may be adjusted in response to visual inspection of the orthotic when located in the mouth of the patient.

It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

DETAILED DESCRIPTION

Figure 1:
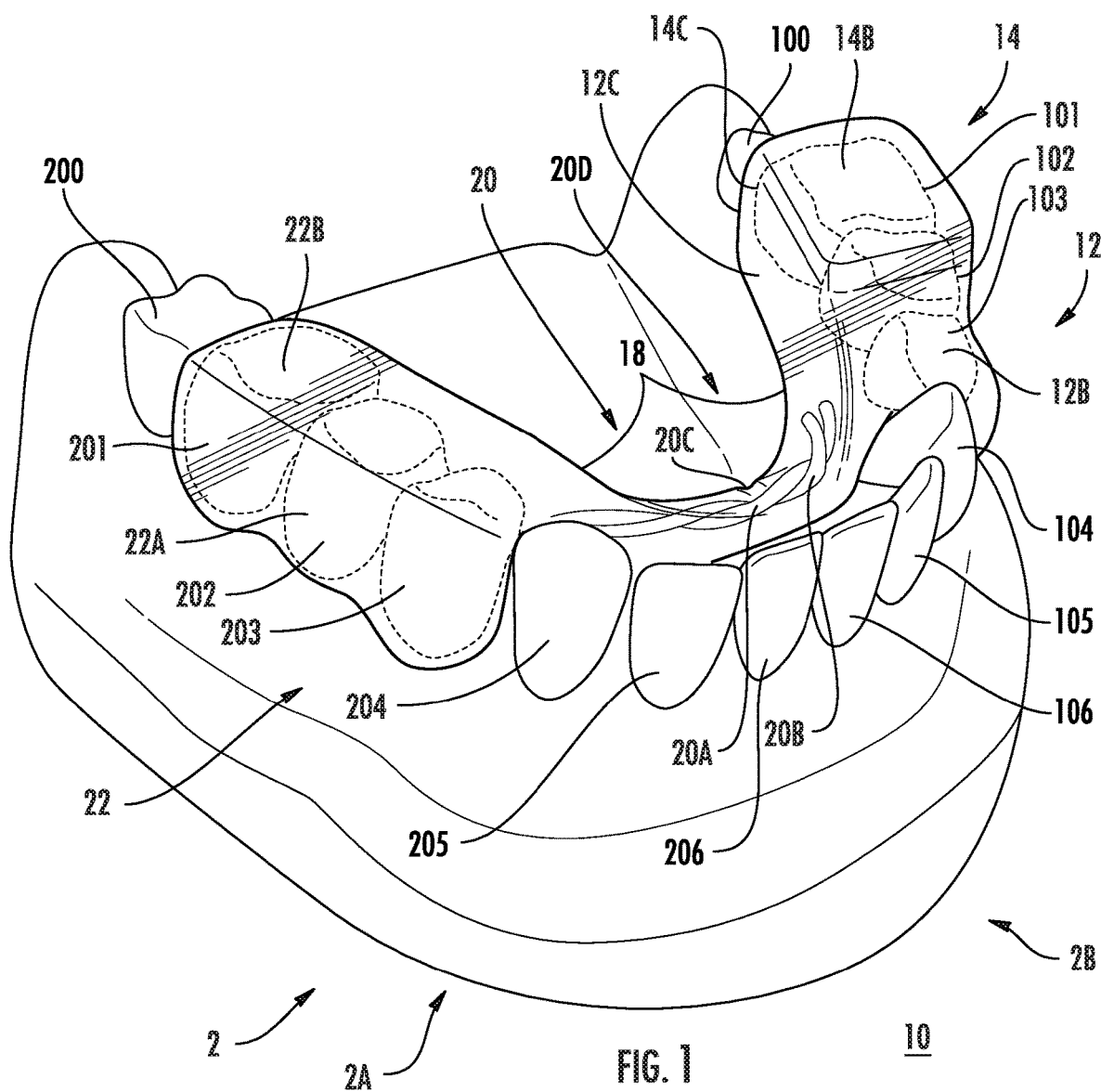
FIG. 1 is a perspective view of an orthotic positioned along the mandible.
Figure 2:
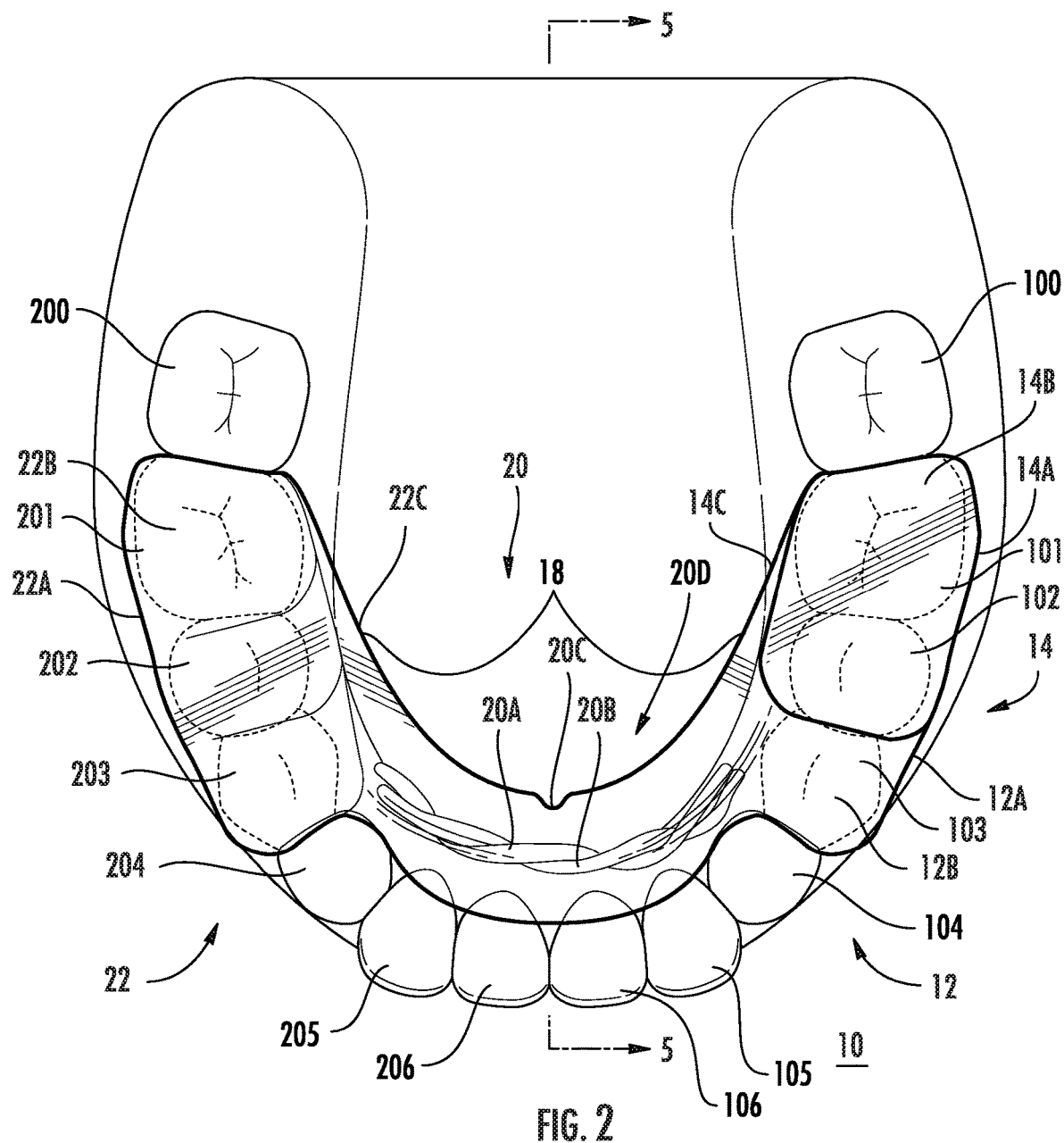
FIG. 2 is a top plan view of the orthotic positioned along the mandible of FIG. 1.

The accompanying drawings, which are incorporated in and constitute a part of the specification, illustrate embodiments of the disclosure and, together with a general description of the disclosure given above, and the detailed description of the embodiment(s) given below, serve to explain the principles of the disclosure.

Embodiments of the present disclosure are described in detail with reference to the drawings, in which like reference numerals designate identical or corresponding elements in each of the several views.

As used herein, the term "clinician" refers to a doctor, nurse, or other care provider and may include support personnel. The term "patient" refers to an individual being treated by a clinician. The term "distal" refers to the portion of the component being described which is further from a clinician, while the term "proximal" refers to the portion of the component being described which is closer to the clinician. The term "left" refers to the left portion of an anatomical structure, such as a mandible, as viewed by a clinician. The term "right" refers to the right portion of an anatomical structure as viewed by the clinician. The term "parafunctional" is defined herein to refer to habits such as bruxism (e.g., clenching of the teeth or jaw), and other habits which are unrelated to eating or speaking.

As will be described in detail below, provided are embodiments of an orthodontic insert or orthotic. The orthodontic insert includes a left portion, a right portion, and a lingual portion. The orthotic may be inserted into a patient's oral cavity (hereinafter "mouth") and retained in the mouth for varying periods of time. In embodiments, the orthotic may be attached to an upper portion of the mouth, along the maxilla. In additional embodiments, the orthotic may be attached to a lower portion of the mouth, along the mandible. As a clinician or the patient positions the orthotic in the patient's mouth, the left and right side of the orthotic are inserted into the mouth, and the clinician or patient holds the lingual portion of the orthodontic insert. The individual then applies pressure to seat the orthotic in the mouth of the individual.

Referring initially to FIGS. 1-7, one embodiment of an orthotic is shown, and designated generally 10. For purposes of clarity, the orthotic 10 will be described as associated with the mandible of a patient, however the orthotic 10 may likewise be adapted to be positioned along the maxilla of the patient. The orthotic 10 includes a left portion 22, a lingual portion 20, and a right portion 12. An occlusal plane 4 is defined by teeth attached to the upper surface of a mandible 2, further defining a left occlusal plane 4A and a right occlusal plane 4B. The lingual portion 20 is dimensioned to contour an arch 18 defined by the mandible. When inserted into the patient's mouth, the orthotic 10 attaches and is positioned adjacent to the mandible 2.

The left portion 22 includes an outer portion 22A, an upper portion 22B, and an inner portion 22C. The outer portion 22A, upper portion 22B, and inner portion 22C define a left arch which is dimensioned to align with contours of teeth located along the left portion 2A of a patient's mouth. The left arch extends along the upper surface of the left occlusal plane 4A between a left first molar 201 and a left first bicuspid 203. It is contemplated that in embodiments, the left arch may extend between a left cuspid 204 and a left second molar 200 or varying positions therebetween. The upper portion 22B and the inner portion 22C connect to a left portion of the lingual portion 20.

The lingual portion 20 extends along the arch defined by the mandible 2 between the left first bicuspid and a second portion of the right first bicuspid. The lingual portion 20 includes lingual arch 18 which encloses a first wire 20A and a second wire 20B. The first and second wire 20A, 20B are braided in a helical fashion to support the lingual arch 18, thereby applying forces in opposite directions when forces are received by either the left portion 22 or the right portion 12 of the orthotic 10. The first and second wire 20A, 20B additionally apply counter forces to torsional forces applied to the orthotic 10 along either the left portion 22 or right portion 12. The lingual portion 20 connects to the right portion 12 of the orthotic 10. The first and second wire 20A, 20B are constructed of stainless steel. In embodiments the first and second wire 20A, 20B is constructed of a material with greater rigidity than the material selected to enclose the first and second wire 20A, 20B. It is further contemplated that, in embodiments a resilient member e.g., may be located in place of the first and second wire 20A, 20B.

The lingual portion 20 further defines a lingual guide plane 20D. The lingual guide plane 20E is offset from the anterior portion of the teeth located along the arch 18 of the patient's mandible. As a result, the lingual portion 20 does not come into contact with the anterior portion of the patient's teeth, thereby reducing the potential to reposition the right and left cuspids (204, 104), lateral incisors (205, 105), and central incisors (206, 106). Additionally, due to the offset between the lingual portion 20 and the anterior portion of the patient's teeth, the chance of gingival irritation is also reduced. The lingual guide plane 20D redirects the patient's tongue when the tongue is advanced toward the lingual portion 20.

The lingual guide plane 20D further defines an indent 20C located along the lingual portion 20. More particularly, the indent 20C is located along the lingual portion 20 between the central incisors (206, 106) of the patient when the orthotic 10 is located in the patient's mouth. The indent 20C is configured to receive a lingual frenulum of the patient when the orthotic 10 is located in the patient's mouth.

The right portion 12 includes an outer portion 12A, an upper portion 12B, and an inner portion 12C. The outer portion 12A, upper portion 12B and inner portion 12C define a right arch which is dimensioned to align with a contour of teeth located along the right portion 2B of the mandible 2. The right arch extends along an upper surface of the right occlusal plane 4B between a right first molar 101 and a portion of a right first bicuspid 103. It is contemplated that in embodiments, the right arch may extend between a right cuspid 104 and a right second molar 100, or varying positions therebetween. The upper portion 12B and the inner portion 12C connect to a right portion of the lingual portion 20.

Figure 3:
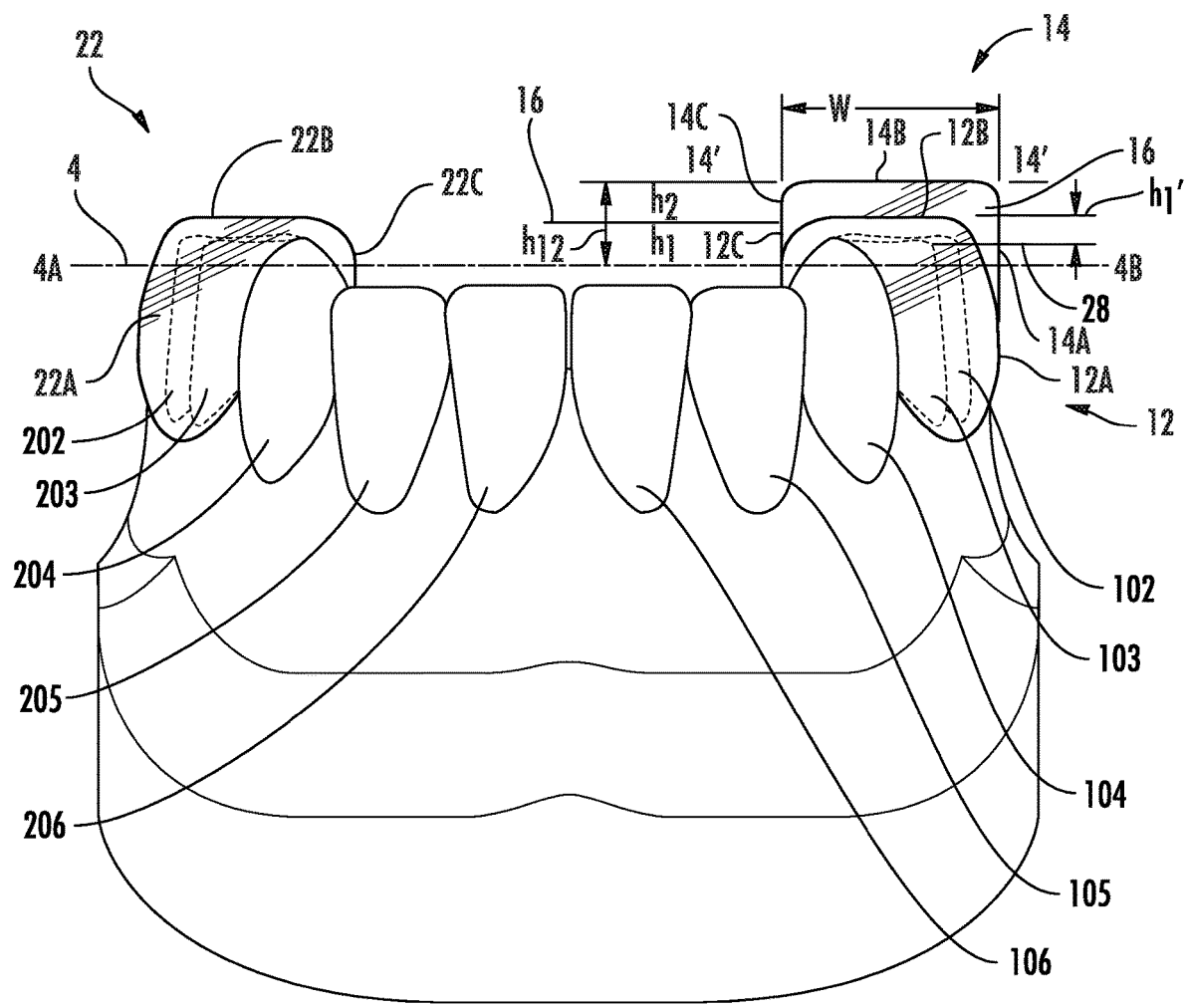
FIG. 3 is a front plan view of the orthotic positioned along the mandible of FIG. 1.
Figure 4:
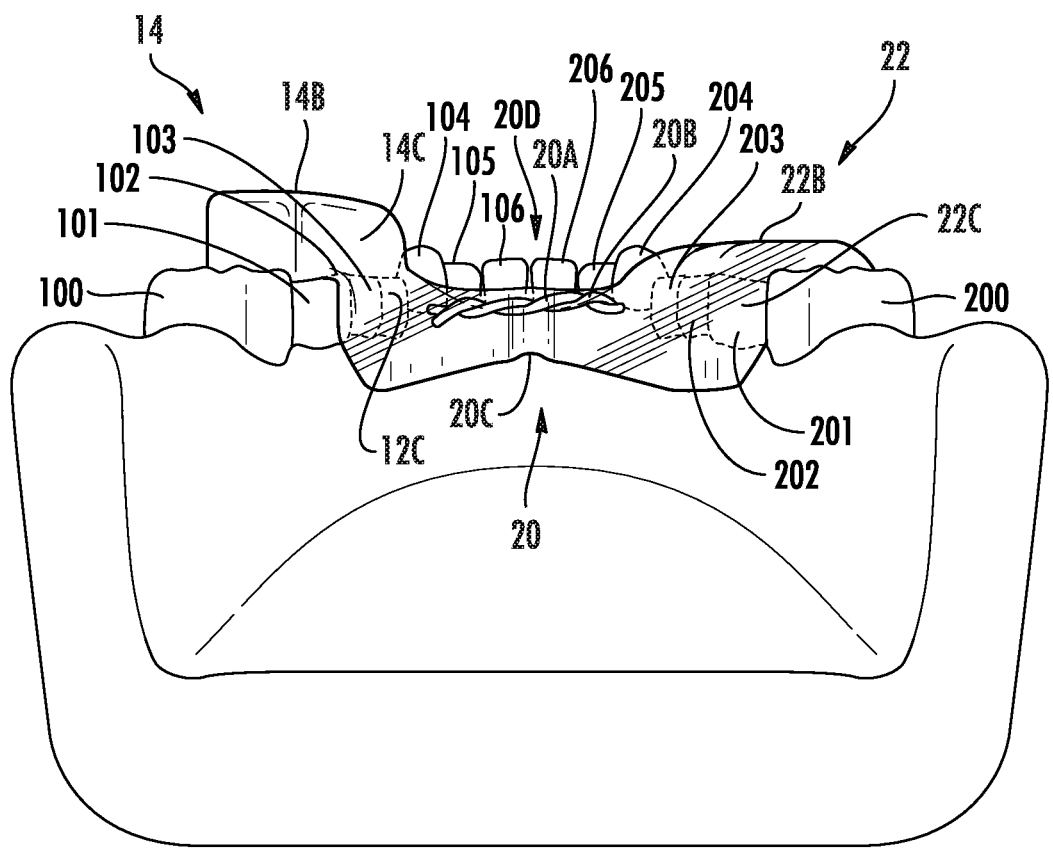
FIG. 4 is a rear plan view of the orthotic positioned along the mandible of FIG. 1.

A bite block or block 14 is positioned above the right portion 12 and defines an augmented occlusal plane 14' with respect to right occlusal plane 4B as shown in FIG. 3. The block 14 extends between at least a portion of the right occlusal plane 4B upward a distance h12=h1+h2 toward the patient's maxillary (not shown), thereby defining a portion of the augmented occlusal plane 14', the augmented occlusal plane 14' extending parallel to the occlusal plane 4B. The block 14 includes an outer portion 14A, an upper portion 14B and an inner portion 14C. The block 14 extends from the upper portion 12B a predetermined distance h2 toward the maxillary bone "A". The upper surface 22B of the left portion 22 and the upper surface 12B of the right portion 12 define a plane positioned to extend a distance h1' above an irregular surface 28 defined by teeth of a patient. In embodiments, the predetermined distance h2 which the block 14 extends toward the maxilla may be between two to seven millimeters.

As known in the art, not all patients who require the orthotic device 10 will have the normal number of teeth and the orthotic 10 may be applied to situations where the patient is missing teeth. It is known in the art that patients who have undergone orthodontic treatment may present with only one premolar. In addition, some patients do not have erupted third molars. Accordingly, for example, the third molar teeth are not shown in FIGS. 1-7. The upper surface 22B of the left portion 22 and the upper surface 12B of the right portion 12 defining a plane positioned to extend above irregular surface 28 defined by teeth of a patient extend at least above the region of the mandible of a patient devoted to supporting a first molar 201, 101, a second bicuspid 202, 102 and a portion of a first bicuspid 203, 103 of a patient. Thus, the bite block 14 may be disposed only along the upper surface 22b of the left portion 22 and extends above the region of the mandible of a patient devoted to supporting a first molar 201 a second bicuspid 202 and a portion of a first bicuspid 203 of a patient, whether or not the patient has each of those teeth present. Alternatively, the bite block 14 may be disposed only along the upper surface 12b of the right portion 12 and extends above the region of the mandible of a patient devoted to supporting a first molar 101, a second bicuspid 102 and a portion of a first bicuspid 103 of a patient, whether or not the patient has each of those teeth present.

The orthotic 10 is fabricated with a standard block 14 that is five millimeters in height h1+h1' unless a different size block 14 is requested based on the patient's oral vertical dimensions. A person who has a collapsed vertical occlusal dimension from dental attrition, may require a seven millimeter block to compensate for the lost vertical dimension. Alternatively, a person with little to no occlusal vertical dimension loss may require a two millimeter block. After fabrication, the block can be reduced with dental burs or increased with dental acrylic if necessary. It is contemplated that in embodiments, the augmented occlusal plane may be angled such that the augmented occlusal plane tilts, or is angled relative to the occlusal plane. An augmented angle may be necessary to accommodate the opposing dentition and can be assessed during fabrication with a model of the counter arch. The block bite plane 16 is configured to define an occlusal plane for engaging the opposing lingual and buccal cusps of the first molar and second premolar. The occlusal plane angle from mesial to distal, or from lingual to buccal, may be altered to accommodate the opposing cusps.

The upper portion 12B extends between a right first molar 101 to a portion of a right first bicuspid 103. The width of the upper portion 12B is defined by the width of the occlusal plane associated with the upper portion 12B, e.g., the right first molar 101, the right second bicuspid 102 and the right first bicuspid 103. It is contemplated that, in embodiments, the upper portion 12B may be wider or narrower than the portion of the occlusal plane 4B above the respective tooth or teeth which the upper portion 12B is positioned above.

Depending on the needs of the patient, the block 14 may be adjusted or augmented by the clinician. For example, to adjust the height during delivery and/or during treatment, the clinician may remove material from the block 14 by grinding, cutting, or otherwise removing material from the outer portion 14A, the upper portion 14B, or the inner portion 14C. Alternatively, the clinician may add material to the outer portion 14A, the upper portion 14B, or the inner portion 14C to increase either the height h1'+h2 or width W of the block 14. Material may be added to more accurately define the augmented occlusal plane defined by the block 14, or to repair the block 14 should deformation occur while used by the patient.

Figure 5:
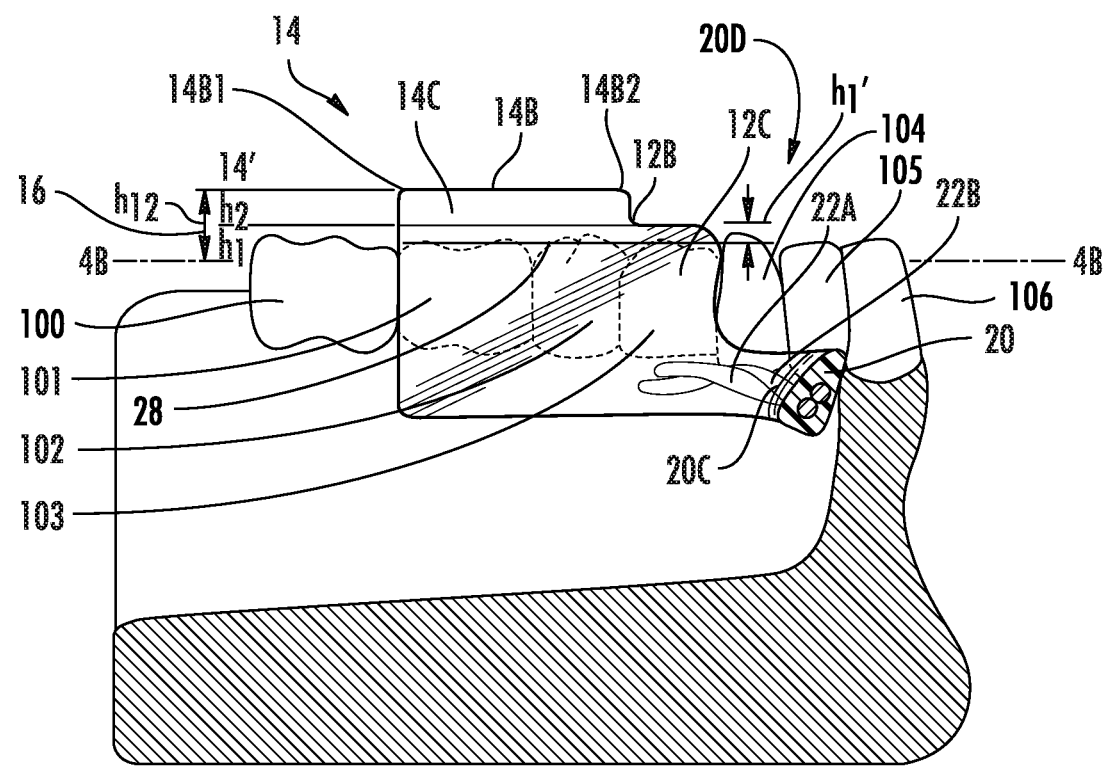
FIG. 5 is a cross-sectional view of the orthotic positioned along the mandible, taken along section line 5-5 of FIG. 2.
Figure 6:
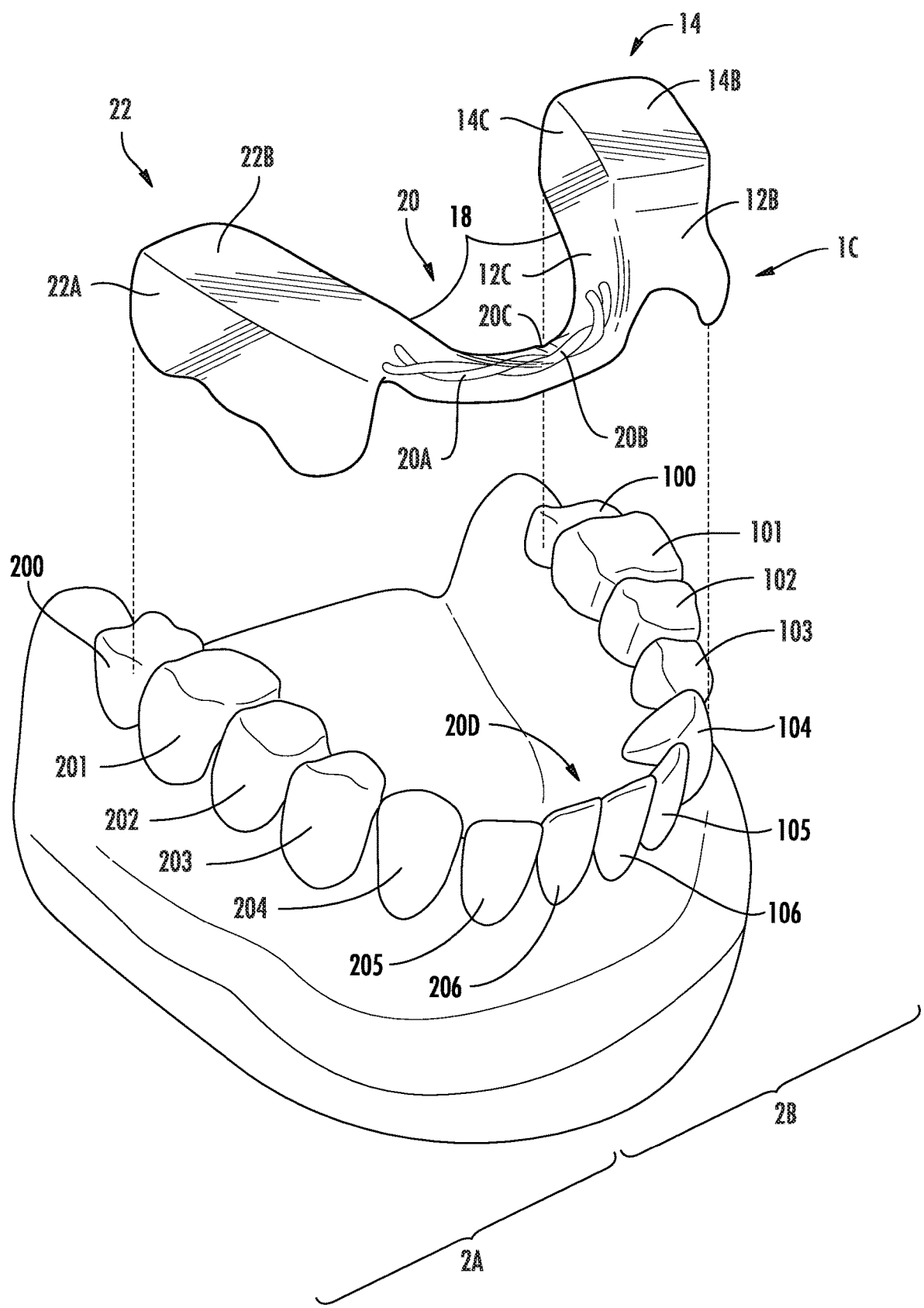
FIG. 6 is an exploded perspective view, with parts separated, of the orthotic and mandible of FIG. 1.
Figure 7:
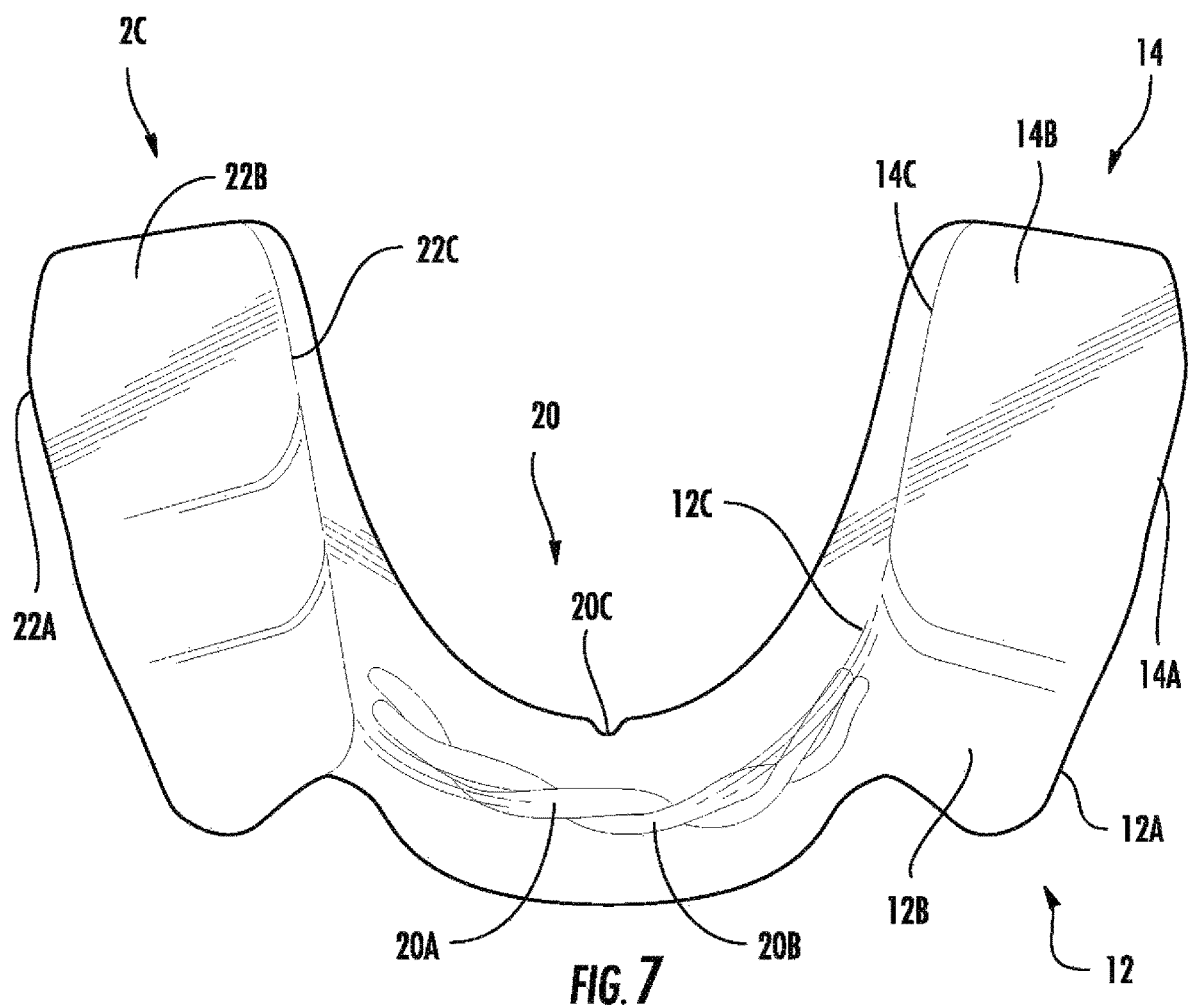
FIG. 7 is a top plan view of the orthotic of FIG. 1.

As best shown in FIGS. 1, 2, 3, 5 and 6, and most particularly in FIG. 5, the position of the upper portion 14B of the block 14 extending from position 14B1 at the rear vertical surface of first molar 101 to position 14B2 at a portion of first bicuspid 103, and thus above the first molar 101, the second bicuspid 102, and the portion of the first bicuspid 103, aligns the block 14 with a fulcrum of the maxillary suture system which is defined by motion of maxillary bone relative to the mandibular bone. As a result, when a patient applies force by biting on the block 14, the maximum amount of force is received by the block 14, and the maximum counter-force is received by teeth opposing the block 14, e.g., a first molar, a second bicuspid, and a portion of a first bicuspid positioned on the maxillary bone (not shown) directly above the block 14.

The left portion 22, lingual portion 20, and right portion 12 may be fabricated from dental acrylic, methyl methacrylate, pressure molded material, resin polymers, or other similar materials. Additionally, the left portion 22, lingual portion 20, and right portion 12 may be fabricated of materials capable of use in three-dimensional (3D) printing such as acrylonitrile butadiene styrene (ABS) plastic, thermoplastics such as polylactic acid, polyamide, polycarbonate, and/or other materials known in the art for use in 3D printing. In embodiments, it is contemplated that the orthotic 10 may be fabricated with other similar compatible materials. The first and second wire 20A, 20B are fabricated of surgical steel, or other similar materials.

During manufacture, an impression is taken of the patient's teeth, along the mandible bone. The impression is then used to create a mold model to form the orthotic 10. Prior to hardening of the dental acrylic, the first and second wire 20A, 20B are twisted about each other into a helical shape. The first and second wire 20A, 20B are subsequently placed into the dental acrylic, and are positioned along the lingual portion 20. A clinician may add or remove material to and from the block 14 as desired during the duration of the patient's treatment.

While located in the patient's mouth and while a parafunctional occlusal force is applied (hereinafter "force"), the block 14 receives force on the upper portion 14B when the patient bites down, intercepting forces which would normally be received by the patient's teeth along the mandibular bone. As a result, the force is distributed from the block 14 to the teeth positioned near the block along the mandibular bone, e.g., the right first molar 101, second bicuspid 102, and the portion of the first bicuspid 103.

Additionally, as the patient bites down to the block 14, a parafunctional occlusal counter-force (hereinafter "counter-force") is applied by the block 14 to opposing teeth which come in contact with the block 14 along the maxillary bone, e.g., a right first molar, second bicuspid, and a portion of a first bicuspid positioned along the maxillary bone (not shown). As a result, force is received along the augmented occlusal plane 14' and is focused along a subset of teeth positioned along the maxillary bone and mandible bone.

The concentration of force causes the patient to realize, either consciously or subconsciously, the application of force to the augmented occlusal plane 14'. Subsequently, the patient reduces or eliminates the application of force to the augmented occlusal plane 14', which reduces stress applied to the patient's teeth as well as mandibular condyles. Additionally, teeth located along the mandible are prevented from coming into contact with teeth located along the maxilla, with the only occlusal contact being between the block 14 and teeth located along the maxilla opposing the block. Thus, the bite block 14 reduces the contact points between the mandibular teeth and the maxillary teeth. Further, as a result of the reduction of force applied to the mandibular condyles, the associated articular discs receive reduced forces which allow the articular discs to decompress.

As best shown in FIGS. 1, 2, 4 and 5, the lingual guide plane 20D allows the tongue (not shown) to advance to an anterior position without being blocked by the acrylic that forms the lingual arch 18 around the braided wires 20A and 20B. Consequently, the tongue moves forward and up and is removed from the throat. The periodontal ligaments of each maxillary tooth will sense reduced contact only on the bite block, therefore reducing the occlusal forces.

The orthotic 10 can be fabricated in multiple ways. The traditional dental technique of acrylic (methyl methacrylate liquid and polymer) added incrementally on the custom dental model (stone and plaster) is most common. Other dental/orthodontic materials, acrylics and resin polymers may be used to fabricate the orthotic. In addition, the orthotic 10 can be fabricated via additive manufacturing (3D Printing).

In use, a clinician first takes a mold of the patient's teeth. The clinician then uses the mold to create the orthotic 10, the mold being used in conjunction with a block mold to form the block 14 along the orthotic 10. Once the orthotic 10 is created, the clinician provides the orthotic 10 to the patient, and positions the orthotic 10 in the patient's mouth. The orthotic 10 is inserted into the patient's mouth and engages one or more teeth located along the left portion 2A and the right portion 2B of the patient's mandible. Upon visual inspection, the clinician determines whether the block 14 must be extended or shortened. The orthotic 10 is removed from the patient's mouth, and the clinician adds or removes material to the orthotic 10 as desired. The clinician repeats this process until the orthotic 10 is determined to be ready by the clinician.

Figure 8:
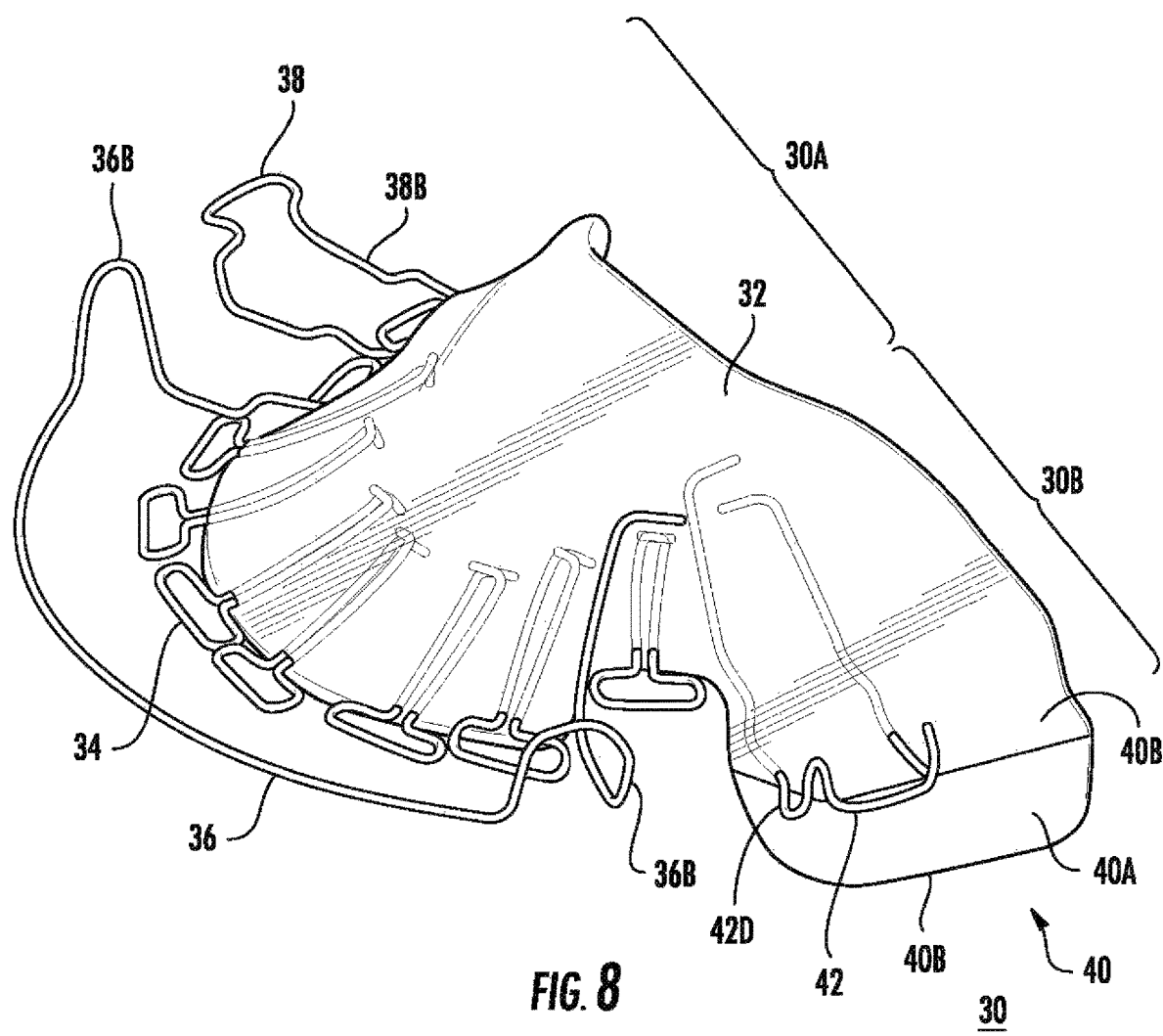
FIG. 8 is a perspective view of a retainer appliance according to the present disclosure.
Figure 9:
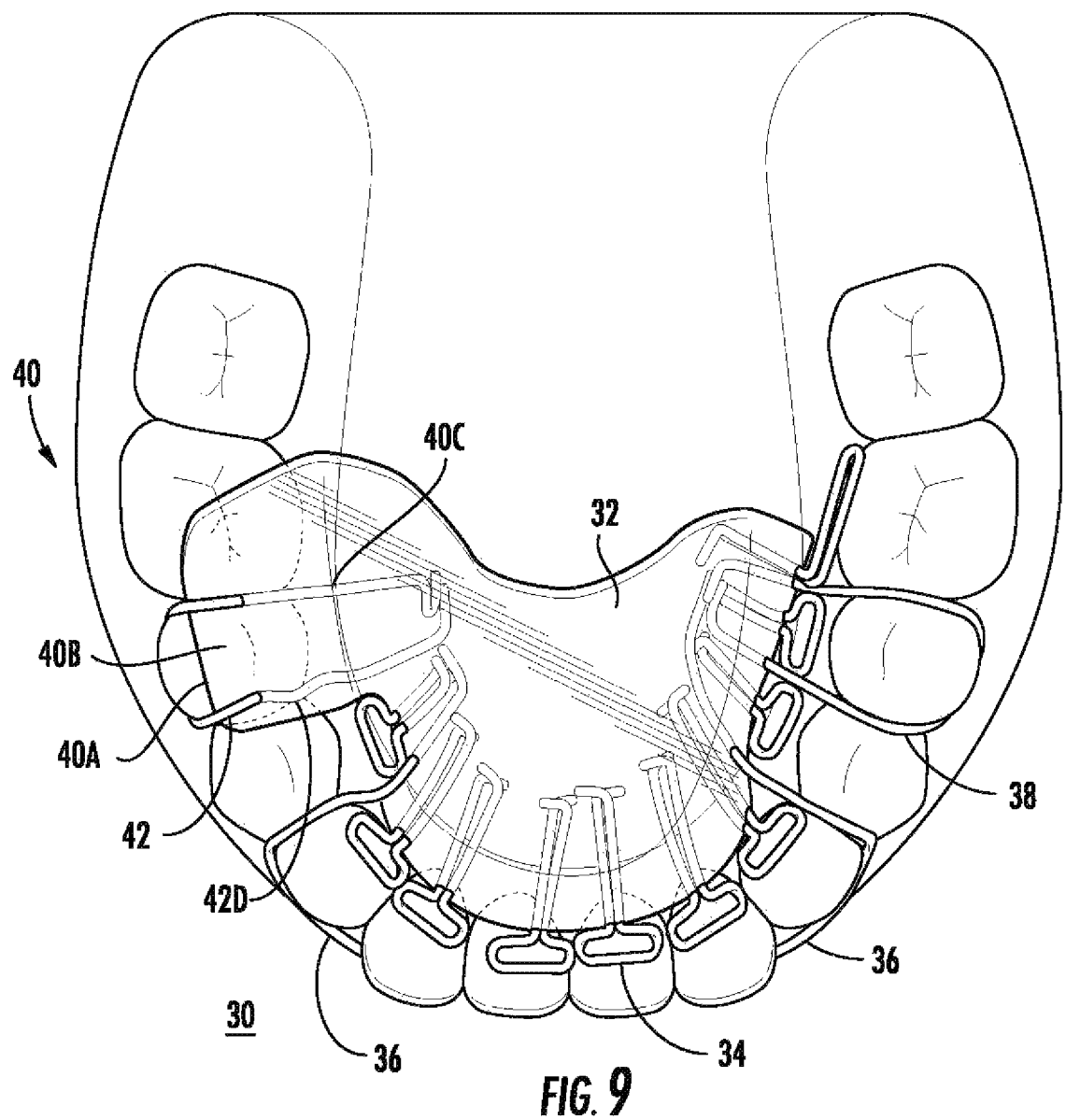
FIG. 9 is a bottom plan view of the retainer appliance of FIG. 9 located along a maxillary bone.

Referring to FIGS. 8 and 9, a retainer appliance is shown and designated generally 30. The retainer appliance 30 includes a retainer body 32, a left clasp 38, a right clasp 42, a plurality of buffer members or springs 34, a frame 36, and a bite block or block 40. The retainer body 32 may be one solid piece, or may be formed by joining a plurality of retainer body pieces (not shown). While the retainer appliance 30 may be configured to be positioned along the maxillary bone or the mandible bone, for purposes of clarity description of the retainer appliance 30 will be with respect to being positioned along the maxillary bone.

The retainer body 32 is dimensioned to contour a roof of the mouth when positioned along a portion of the maxillary bone. Specifically, the retainer body 32 is dimensioned to extend along a portion of the roof of the mouth, maintaining a gap "G" between the retainer body 32 and teeth of the patient. The gap "G" may be a predetermined distance or may vary depending on the needs of the patient. The retainer body may be made of acrylic or other similar biocompatible substances. The retainer body 32 further encloses a portion of the left clasp 38, the right clasp 42, the plurality of springs 34, and the frame 36 (collectively referred to as the retainer members), which extend outward from the retainer body 32. As a result of enclosing portions of the retainer members, the retainer body 32 provides structural support to the retainer members when inserted into the patient's mouth.

The left clasp 38 and the right clasp 42 extend from the retainer body 32 and are dimensioned to maintain placement of the retainer appliance 30 when positioned in the patient's mouth. The left and right clasp 38, 42 both define a left and right arch 38D, 42D, respectively. The left arch 38D is dimensioned to be fitted about one or more teeth, e.g., the first bicuspid, the second bicuspid, the first molar, and/or the second molar positioned along the left portion of the maxillary bone. Likewise, the right arch 42D is dimensioned to be fitted about symmetrically opposing teeth positioned on the right portion of the maxillary bone.

The plurality of springs 34, or T-Flap springs, connect to the retainer body 32 and extend from the body toward the patient's teeth. Specifically, the springs 34 extend between the edge of the retainer body 32 and the patient's teeth, thereby providing structural support to maintain the gap "G" between the retainer body 32 and the patient's teeth, e.g., the left and right second bicuspids, first bicuspids, cuspids, lateral incisors, and central incisors. The springs 34 include support members 34B which support spacers 34A. The support members 34B are partially enclosed by the retainer body 32 and extend outward relative to the retainer body 32 toward the patient's teeth. The spacers 34A are oval shaped, and may be bent as needed by the clinician at delivery or during treatment of the patient.

The frame 36, commonly referred to in the art as a Hawley frame, extends outward from and is partially enclosed by the retainer body 32 at two points. The frame 36 is dimensioned to contour to a front surface of the patient's teeth and apply inward pressure against the patient's teeth toward the retainer body 32. The frame 36 includes two frame clasps 36B which are dimensioned to fit about one or more teeth positioned along the left and right portion of the patient's maxillary bone.

The frame 36 and springs 34 are made of surgical steel, though in embodiments it is contemplated that the frame may be made of other suitable biocompatible materials which allow for deformation by a clinician. Additionally, the retainer body is made of a hard acrylic or other similar biocompatible plastic or composite.

The block 40 is positioned on the right side of the retainer appliance 30 and extends from the right side of the retainer body 32 toward the patient's teeth. The block 40 encloses a second portion of the right clasp 42. The block further includes an outer portion 40A, a lower portion 40B, an inner portion 40C, and an maxillary portion 40D. The maxillary portion 40D extends along a portion of the maxillary bone, and is configured to be in contact with one or more teeth associated with the maxillary bone. Specifically, the maxillary portion 40D defines an arch which contours to one or more of the patient's teeth when the retainer appliance 30' is positioned in the patient's mouth. As shown, the maxillary portion 40D extends along the right first molar, second bicuspid, and a portion of the first bicuspid. It is contemplated that, in embodiments, the maxillary portion 40D may extend along a greater or lesser portion of the patient's teeth located along the maxillary bone.

In use, similar to fabrication of the orthotic 10, the clinician first takes a mold of the patient's teeth. Once the retainer appliance 30 is created, the clinician provides the retainer appliance 30 to the patient, and positions the retainer appliance 30 in the patient's mouth. The retainer appliance 30 is inserted into the patient's mouth and engages one or more teeth located along the left portion and the right portion of the patient's maxilla. Upon visual inspection, the clinician determines whether the block 40 must be extended or shortened. The retainer appliance 30 is removed from the patient's mouth, and the clinician adds or removes material to the retainer appliance 30 as desired. The clinician repeats this process until the retainer appliance 30 is determined to be ready by the clinician.

For a detailed discussion of the construction of a retainer appliance, reference may be made to U.S. Pat. Nos. 7,314,372, and 7,357,635, the entire disclosures of which are hereby incorporated by reference.

Figure 10:
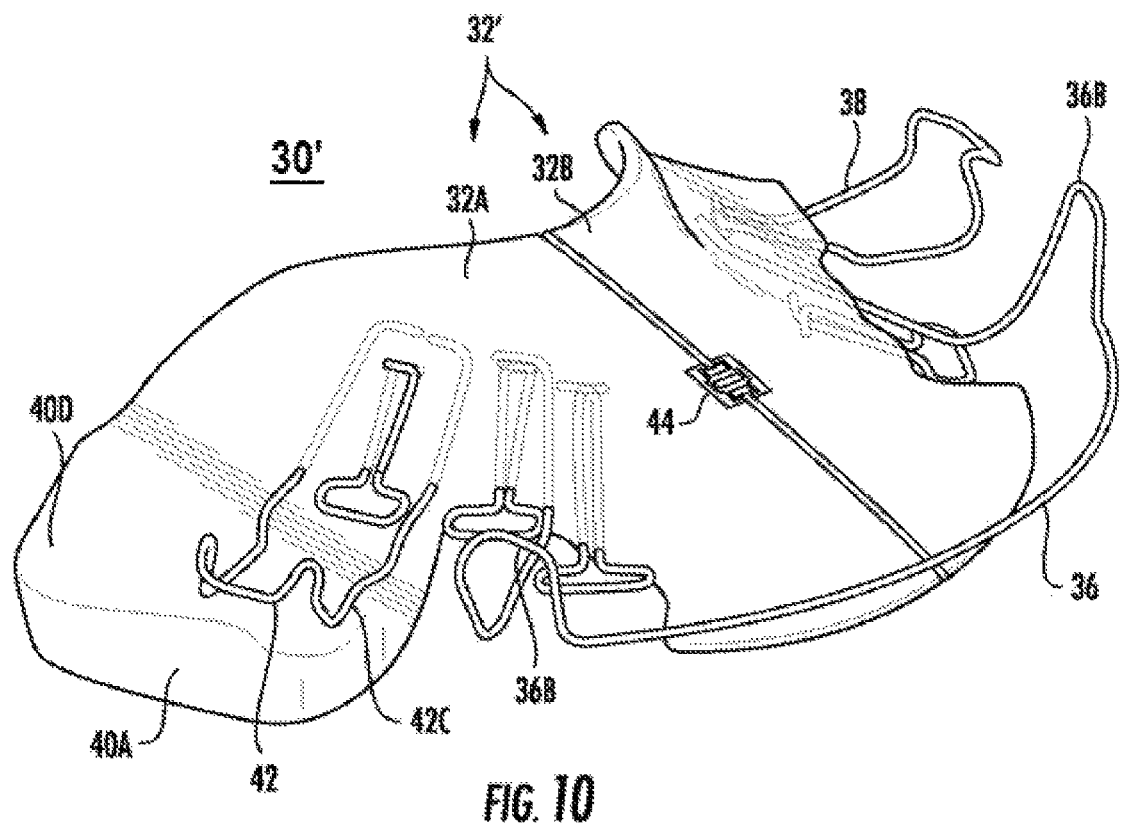
FIG. 10 is a perspective view of another retainer appliance according to the present disclosure.
Figure 11:
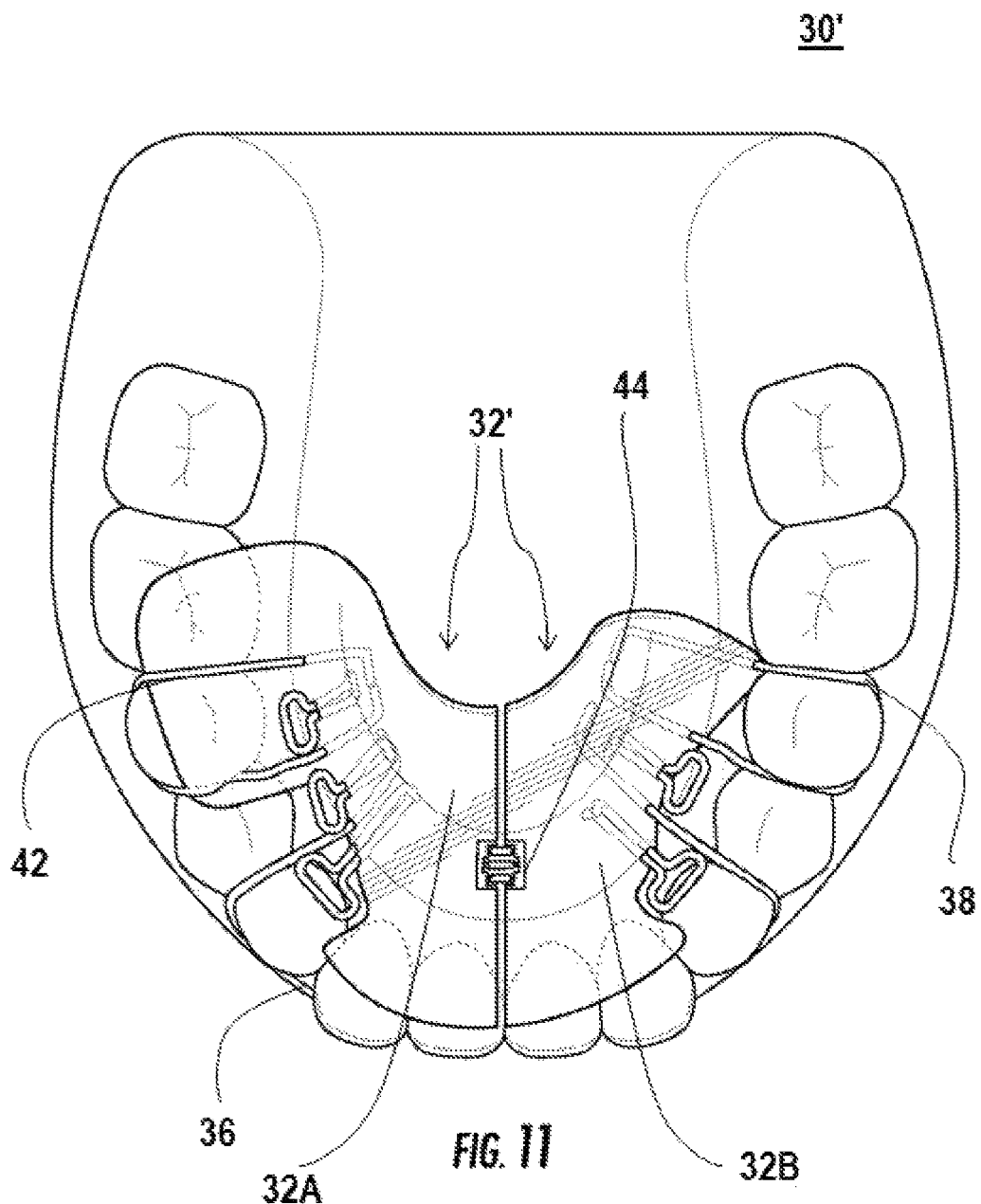
FIG. 11 is a bottom plan view of the retainer appliance of FIG. 10 located along a maxillary bone.

Referring to FIGS. 10 and 11, an alternative embodiment of the retainer appliance of FIG. 9 is shown, and designated generally 30'. The retainer appliance 30' includes a retainer body 32' which includes a left portion 32A and a right portion 32B. The left and right portions 30A, 30B are connected by the frame 36 and a spacer mechanism 44. The spacer mechanism 44 may include a screw 44A which can be actuated, increasing or decreasing a second gap "G2" between the left portion 30A and the right portion 30B.

Figure 12:
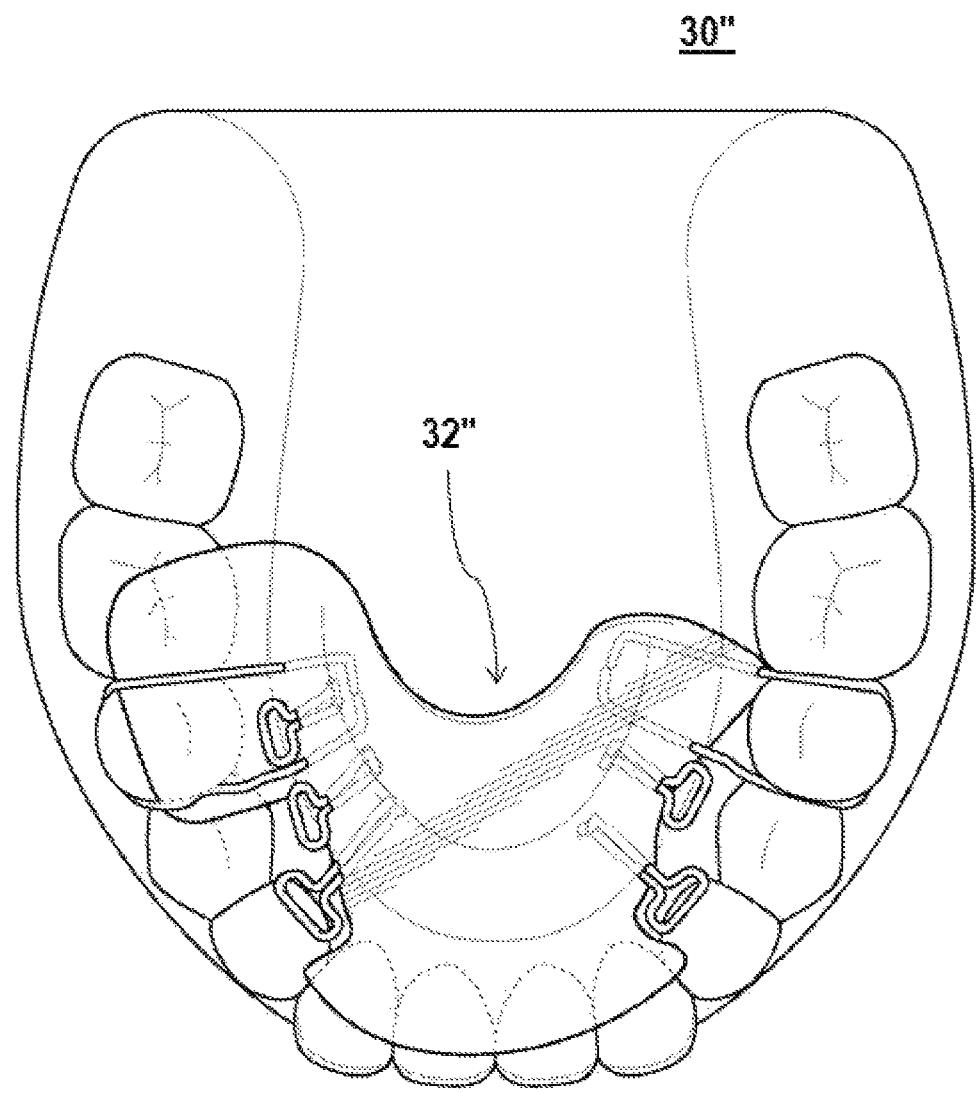
FIG. 12 is a perspective view of another retainer appliance according to the present disclosure.

Referring to FIG. 12, an alternative embodiment of the retainer appliance of FIG. 9 is shown, and designated generally 30". A retainer body 32" extends along a portion of the roof of the patient's mouth. The retainer appliance 30" includes a retainer body 32" which is dimensioned to be positioned flush against one or more of the patient's teeth. As a result, the retainer body 32" extends along a portion of the roof of the mouth, thereby maintaining the position of the retainer appliance 30" relative to the patient's teeth without the need for springs 34.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. An oral orthotic device comprising:
   a left portion including an upper surface;
   a right portion including an upper surface;
     the upper surface of the left portion and the upper surface of the right portion defining a plane positioned to extend above an irregular surface defined by teeth of a patient,
   a bite block to extending from the upper surface of one of the left portion or the right portion a distance above the plane such that the bite block is disposed on the oral orthotic device exclusively on either the left portion or the right portion; and
   a lingual portion coupled to the left portion and to the right portion wherein the lingual portion includes a lingual arch defined by a mandible between a left first bicuspid and a right first bicuspid of a user of the orthotic device, the lingual arch enclosing a helically configured wire therein to support the lingual arch between the left first bicuspid and the right first bicuspid of the user of the orthotic device.

2. The orthotic device of claim 1, wherein the bite block includes an upper portion that extends upward between two and seven millimeters from the plane positioned to extend above the irregular surface defined by teeth of a patient.

3. The orthotic device of claim 1, wherein the helically configured wire is a first wire and the lingual arch further comprises a helically configured second wire braided about the first wire.

4. The orthotic device of claim 1, wherein the left portion defines a left arc and the right portion defines a right arc, wherein the left arc is configured to contour to teeth located along a left portion of a mandible, and the right arc is configured to contour to teeth located along a right portion of the mandible.

5. The orthotic device of claim 4, wherein the left arc and right arc are dimensioned to contour teeth located in a mouth of a patient.

6. The orthotic device of claim 1, wherein the upper surface of the left portion and the upper surface of the right portion defining a plane positioned to extend above an irregular surface defined by teeth of a patient extend at least above the region of the mandible of a patient devoted to supporting a first molar, a second bicuspid and a portion of a first bicuspid of a patient.

7. The orthotic device of claim 6,
   wherein the bite block is disposed only along the upper surface of the left portion and extends at least above the region of the mandible of a patient devoted to supporting a first molar, a second bicuspid and a portion of a first bicuspid of a patient or
   wherein the bite block is disposed only along the upper surface of the right portion and extends at least above the region of the mandible of a patient devoted to supporting a first molar, a second bicuspid and a portion of a first bicuspid of a patient.

8. A method of utilizing an orthotic device, the method comprising:
   providing an orthotic device to a patient, the orthotic device having a left portion, a right portion, a lingual portion, and a bite block configured and disposed exclusively on one of the left portion or the right portion to extend over a subset of teeth of a patient along the mandibular bone of the patient;
   positioning the orthotic device in a mouth of the patient; and
   applying pressure to the orthotic device to cause the left portion and the right portion to engage teeth located along a mandible of the patient such that the bite block causes reduction of force wherein the lingual portion includes a lingual arch defined by a mandible between a left first bicuspid and a right first bicuspid of a user of the orthotic device, the lingual arch enclosing a helically configured wire therein to support the lingual arch between the left first bicuspid and the right first bicuspid of the user of the orthotic device received by the subset of teeth along the mandibular bone.

9. The method of claim 8, further comprising:
- removing the orthotic device from the mouth of the patient; and
- augmenting or decreasing a height of the bite block, wherein the height of the bite block is adjusted in response to visual inspection of the orthotic when located in the mouth of the patient.

10. The method of claim 8, wherein the reduction of force received by the subset of teeth along the mandibular bone includes the bite block preventing teeth along the mandible of the patient from contacting the teeth of the patient located along the maxilla of the patient.

11. The method of claim 10, wherein the bite block preventing teeth along the mandible of the patient from contacting the teeth of the patient located along the maxilla of the patient includes the bite block reducing force received by the teeth of the patient located along the maxilla of the patient.

12. The method of claim 11, wherein the bite block reducing force received by the teeth of the patient located along the maxilla of the patient is effected by a reduction in contact points between the teeth of the patient located along the mandible of the patient and the teeth of the patient located along the maxilla of the patient due to the presence of the bite block.

13. The method of claim 8, wherein the reduction of force received by the subset of teeth along the mandibular bone includes the bite block reducing force applied to the mandibular condyles of the patient.

14. The method of claim 13, wherein the bite block reducing force applied to the mandibular condyles of the patient includes the articular discs of the patient associated with the mandibular condyles of the patient receiving reduced forces thereby enabling decompression of the articular discs of the patient.

* * * * *